United States Patent
Herklotz et al.

(10) Patent No.: US 6,672,841 B1
(45) Date of Patent: Jan. 6, 2004

(54) PUMPING AND METERING DEVICE

(75) Inventors: Martin Herklotz, Griesheim (DE); Hans-Peter Schneider, Neu-Anspach (DE); Jörg Bigalke, Frankfurt (DE); Rainer Dönig, Frankfurt (DE); Jürgen Häcker, Weinsberg (DE)

(73) Assignee: Fresenius Medical Care Deutschland GmbH (DE)

( * ) Notice: Subject to any disclaimer, the term of this patent is extended or adjusted under 35 U.S.C. 154(b) by 0 days.

(21) Appl. No.: 09/308,914

(22) PCT Filed: Mar. 26, 1998

(86) PCT No.: PCT/EP98/01792

§ 371 (c)(1),
(2), (4) Date: Nov. 18, 1999

(87) PCT Pub. No.: WO99/17019

PCT Pub. Date: Apr. 8, 1999

(30) Foreign Application Priority Data

Sep. 26, 1997 (DE) ......................... 197 42 632

(51) Int. Cl.[7] ................................. F04B 49/00
(52) U.S. Cl. ............... 417/46; 417/386; 417/388; 417/390; 417/395; 60/539; 60/535
(58) Field of Search .................. 417/46, 383, 385, 417/386, 387, 388, 390, 395; 60/534, 535

(56) References Cited

U.S. PATENT DOCUMENTS

| | | | |
|---|---|---|---|
| 3,428,042 A | * 2/1969 | Chesnut ................... 600/17 |
| 3,771,694 A | 11/1973 | Kaminski .................. 222/644 |
| 4,303,376 A | 12/1981 | Siekmann ................... 417/360 |
| 4,468,222 A | 8/1984 | Lundquist .................. 604/153 |
| 4,624,625 A | * 11/1986 | Schrenker .................. 417/20 |
| 4,828,464 A | * 5/1989 | Maier et al. ................ 417/388 |
| 5,056,036 A | 10/1991 | Van Bork ................... 700/282 |
| 5,074,755 A | * 12/1991 | Vincent .................... 417/18 |
| 5,201,636 A | * 4/1993 | Mikulski ................... 417/18 |
| 5,249,932 A | * 10/1993 | Van Bork ................... 417/386 |

FOREIGN PATENT DOCUMENTS

| | | |
|---|---|---|
| DE | 27 60 412 | 12/1977 |
| DE | 28 38 177 | 3/1980 |
| DE | 31 39 925 | 7/1983 |
| DE | 33 20 386 | 12/1984 |
| DE | 296 08 950 | 8/1996 |
| EP | 0 376 497 | 7/1990 |
| EP | 0 641 935 | 3/1995 |
| JP | 62-135675 | 6/1987 |

* cited by examiner

*Primary Examiner*—Charles G. Freay
(74) *Attorney, Agent, or Firm*—Kenyon & Kenyon

(57) ABSTRACT

The present invention relates to a pumping device for delivering and metering fluids, in particular medical fluids such as dialysis fluids, with a piston unit having a driving device and a piston and with a membrane unit which has a membrane and a first chamber bordered by the membrane. The pumping device also has a hydraulic unit which has a space to accommodate a hydraulic fluid which is connected to the piston of the piston unit and to the first chamber of the membrane unit. The reliability of metering by such a pumping device is increased by providing a control unit for guaranteeing a predefinable metering rate and/or quantity and also providing a measuring device by means of which the axial position of the piston unit can be determined directly and which can be connected to the control unit.

17 Claims, 3 Drawing Sheets

PUMPING AND METERING DEVICE

FIELD OF THE INVENTION

The present invention relates to a pumping device for delivering, balancing and metering fluids, in particular medical fluids such as blood or dialysis fluids, with a driving device and a piston unit including a piston and a membrane unit having a membrane and a first chamber bordered by the membrane. The pumping device also includes a hydraulic unit having a space to accommodate a hydraulic fluid which is connected to the piston of the piston unit and to the first chamber of the membrane unit.

An important advantage of such a pump system is that the advantages of piston machines can be combined with those of membrane units. The piston unit, which operates as a piston pump, serves as an internal displacement pump which is connected to the membrane of the membrane unit by a hydraulic fluid. The hydraulic fluid is in a closed system and transmits the axial movement of the piston to the membrane, which is moved accordingly in the membrane unit.

BACKGROUND OF THE INVENTION

Precise metering of fluids is important, for example, in the area of dialysis, where fluids with a known composition must be conveyed at precisely definable rates. The dialysis fluids used here are composed of numerous substances, the type and quantity of which must be based on the needs of an adequate and individualized patient treatment. The essential functions of a dialysis machine include pumping the fluid at precisely predetermined metering rates and quantitative determination of the quantities pumped for the purposes of balancing. One disadvantage of the known dialysis systems is that these functions must be executed by different units, which results in heavy and complex machines that are difficult to handle.

A compact metering system is known, for example, from European Patent No. 376,497 from the field of coating semiconductor components, where precise delivery and metering of liquid media is also necessary. A generic pumping device is described here, where a membrane is in contact on one side with a hydraulic fluid in a suitable space. The desired movement of the membrane is accomplished with a piston movement, with the movement of a piston of the piston unit being transmitted to the membrane by the hydraulic fluid. This metering unit is controlled on the basis of the number of pulses per unit of time which are applied to the motor driving the piston. The relationship between the number of pulses per unit of time and the desired delivery head of the pumping device is determined by calibration before use and is used to control the pumping device in operation. One disadvantage of such a procedure is that, for example, due to faulty determination of the required number of pulses, due to variable loads or due to inadequate calibration, there may be a faulty relationship between the number of pulses per unit of time and the delivery head, which makes accurate metering difficult.

OBJECTS OF THE INVENTION

The object of the present invention is to improve upon a pumping device in such a way as to increase the reliability of metering and balancing.

This object is achieved on the basis of a generic pumping device by providing a control unit for controlling a predefinable metering rate and/or quantity as well as a measuring device by means of which the axial position of the piston of the piston unit can be determined directly and which can be connected to the control unit. In this way, it is possible to determine the piston position directly and reliably and, after taking the time into account, the change over time can be determined, with the determination being independent of the functioning and reliability of the drive unit. In addition to these functions of metering and delivery, the device according to the present invention also fulfills the function that the quantity of fluids delivered can be quantified, thus permitting balancing, e.g., during a dialysis treatment. This creates a compact and reliable delivery, metering and balancing system that permits favorable manufacturing and maintenance in addition to offering space and weight advantages. In particular, the system according to the present invention is suitable for hemodialysis, because a performance spectrum with small dimensions is created that makes superfluous the use of additional control and monitoring equipment which would necessitate the patient's stay in a clinic or hospital. Additional fields of application of the pumping device according to the present invention include peritoneal dialysis, hemofiltration and related methods. Owing to the directly determinable position of the piston and the piston speed which can be determined from that, the pumping device according to the present invention permits calculation of all necessary system data, such as the volume delivered or the delivery rate by taking into account the average area of the piston. In addition to the above-mentioned kinematic parameters, the pressure conditions can also be monitored and regulated due to the use of a hydraulic sensor. Moreover, partial volumes can also be detected and adjusted.

It is especially advantageous if the piston has a piston head for delivering the hydraulic fluid as well as a piston shaft and if the measuring device is arranged in such a way that the axial position of the piston shaft can be determined.

The measuring device according to the present invention with which the axial position of the piston and the piston shaft can be determined directly may have optical, electromechanical, and/or electric sensors.

According to a preferred embodiment, a second chamber can be formed by a membrane pump head detachably mounted on the membrane unit, with the second chamber being arranged on the membrane side opposite the first chamber and with the membrane pump head having at least one inlet and at least one outlet.

The second chamber serves as a delivery chamber holding the medium to be delivered, while the first chamber is acted upon by hydraulic fluid to induce a corresponding movement of the membrane.

In the mounted state of the membrane pump head, the second chamber can be directly adjacent to the membrane of the membrane unit. In this case, the membrane is acted upon by fluid from both sides, with the hydraulic fluid being on one side of the membrane and the fluid to be delivered being on the other side of the membrane.

It is especially advantageous if the second chamber is bordered by a membrane which is adjacent to the membrane of the membrane unit when the membrane pump head is in the mounted state. In this case, the two membranes are adjacent to one another, with the movement of the hydraulic fluid first inducing movement in the membrane of the membrane unit, and due to the contact of this membrane with the membrane of the head piece, the fluid to be delivered is introduced into the second chamber or removed from it accordingly. Such a design of the pumping device according to the present invention is advantageous in particular because in this case there are two completely separate systems. Although the pumping device according to the present invention is the delivery unit according to claim 1, for example, the membrane pump head with the membrane serves to seal the medium to be pumped and to separate substances with the device according to the present invention. As a result of this separation of substances, neither the hydraulic fluid nor the medium to be pumped becomes contaminated, but also the parts of the pumping device according to the present invention are neither attacked nor contaminated by the medium to be pumped. In this case, the choice of membrane material of the membrane unit will not depend primarily on the corrosion properties but instead will depend primarily on the criterion of long-term stability.

In another embodiment of the present invention, the inlet and/or outlet of the head piece can be closed off. To that effect, valves or clamps in particular are provided. These have the function of causing the outlet of the head piece to be blocked when the medium to be pumped is being drawn into the second chamber, while the inlet valve is closed and the outlet valve is opened accordingly when the intake medium is being ejected. It is not necessary here for all the fluid in the second chamber to be delivered in the ejection operation. Instead, it is possible for only a quantity of intake fluid corresponding to the maximum possible piston position to be ejected.

It is especially advantageous if the head piece is designed in such a way that it can be used for a single use. While the pumping device according to the present invention serves the function of accurately moving the membrane and thus metering, the head piece has the function of executing the actual delivery of fluid. The exchangeable head piece, which is designed as a disposable article according to the present embodiment and can be mounted on the pumping device, has the advantage that it is not necessary to clean difficultly accessible components such as valves, because the head piece is not reused after a single use. Thus, the membrane of the membrane unit forms the interface of the pumping device with the head piece designed as a disposable article in which the substance transport and delivery of media to and from the patient are to take place. The definite media separation, which prevents direct contact between the media to be pumped and machine system parts in the pumping device according to the present invention, has the effect that impurities cannot enter the dialysis fluid and no dialysis fluid can enter the pumping device due to leakage, for example. Another advantage is that the metering and balancing accuracy of the pumping device is independent of the dimensional accuracy of the head piece, which is designed as a disposable article, because all the components necessary for balancing and metering are provided in the piston pumping device and not in the mountable membrane pump head.

In another embodiment of the present invention, a pressure sensor is provided that is connected to the space of the hydraulic unit. By using such a pressure sensor in the hydraulic unit, an individually adjustable delivery pressure limit and display can be achieved for the system. This is important in particular when the outlet valve of the head piece inadvertently fails to open, for example.

It is especially advantageous if the pressure sensor can be connected to the drive of the piston unit. This makes it possible for the pressure sensor to interrupt pump operation on reaching a limit value to limit the forces introduced into the system.

In another embodiment of the present invention, the driving device of the piston unit includes a linear drive. Examples of suitable linear drives include, for example, eccentric drives, spindle drives and rack and pinion drives as well as pneumatic pistons with compressor drives.

The hydraulic system of the pumping device according to the present invention may have a vent valve, which guarantees that the hydraulic fluid is free of gases. This is especially important because the movements of the piston unit and the membrane can be coordinated accurately only when the transmission medium is incompressible, as is the case with gas-free fluids, for example.

In another embodiment of the present invention, a computer unit is provided and is connected to the measuring device and/or the control unit and it can perform the balancing of the media pumped. Because of the direct determination of the piston position and the determination of the change over time, it is possible to determine the media pumped up to that point, which is necessary for accurate monitoring of the process.

The computer unit can be integrated into the control unit.

To improve handling of the pumping device according to the present invention, the piston unit may be arranged on a chassis.

It is especially advantageous if the membrane of the membrane unit has two membrane layers made of a nonstretching material and an interspace filled with an incompressible medium extending between the two membrane layers, so that the membrane layers have an outward bulge with respect to the interspace. Such a design prevents the disadvantage associated with the elastic membranes known in the past, when there is an unwanted deformation or deflection of the membrane due to the pressure difference between the two sides of the membrane. As a result of this deflection, an exact correlation between the position of the piston of the piston unit and the membrane deflection and thus accurate metering are impossible unless the pressure conditions are always constant. On the other hand, the membrane according to the present invention is always kept in a definite position regardless of the pressure conditions, so that a reproducible correlation between piston movement and quantity delivered is guaranteed.

In another embodiment of the present invention, the membrane layers are arranged with a separation between them by a spacer. With a suitable design of the spacer, this facilitates filling of the interspace between the membrane layers in particular.

Additional details and advantages of the pumping device according to the present invention are apparent from the drawings, which show:

DETAILED DESCRIPTION OF THE PREFERRED EMBODIMENT

Figure 1:
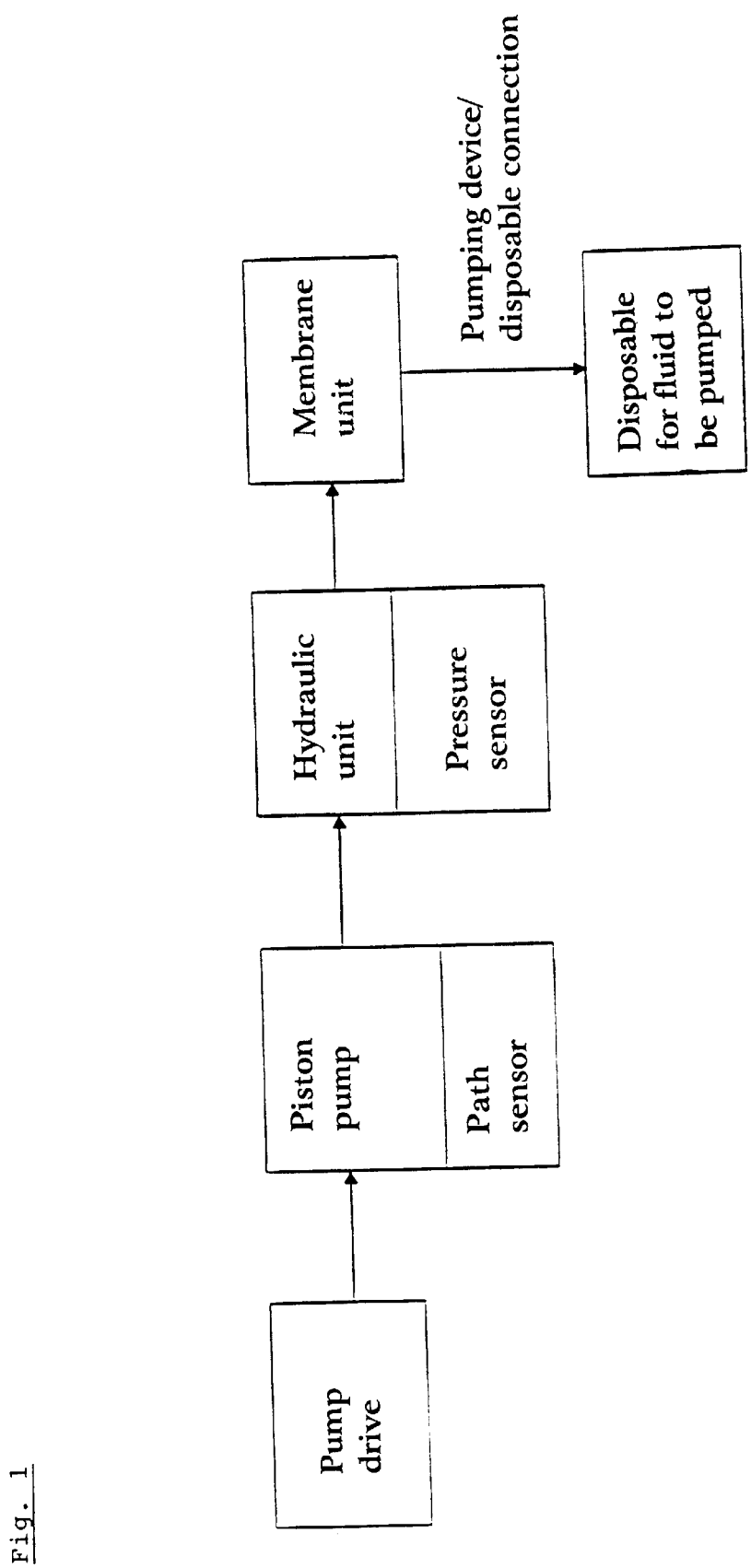
FIG. 1: a schematic diagram of the pumping device according to the present invention.

As FIG. 1 shows, a pump drive which includes a linear drive, for example, drives the piston of a unit which is shown here as a piston pump. The measurement device according to the present invention, which is shown as a path sensor in the embodiment according to FIG. 1, determines the exact position of the piston.

Use of a piston pump as the metering unit is based on the fact that piston pumps are preferred for use as metering pumps because not only is accurate metering possible, but also a simple and flexible adjustment at a new setpoint is also possible.

The hydraulic unit transmits the movement of the piston pump to the membrane unit. The hydraulic unit has a pressure sensor which delivers an alarm signal, for example, or interrupts the piston unit drive directly on reaching a predefinable pressure limit.

According to the present embodiment, a head piece which is characterized as "disposable" can be secured on the membrane unit and is connected to the fluid to be pumped. Thus, direct contact between this fluid and the parts of the pumping device according to the present invention is effectively prevented.

Figure 2:
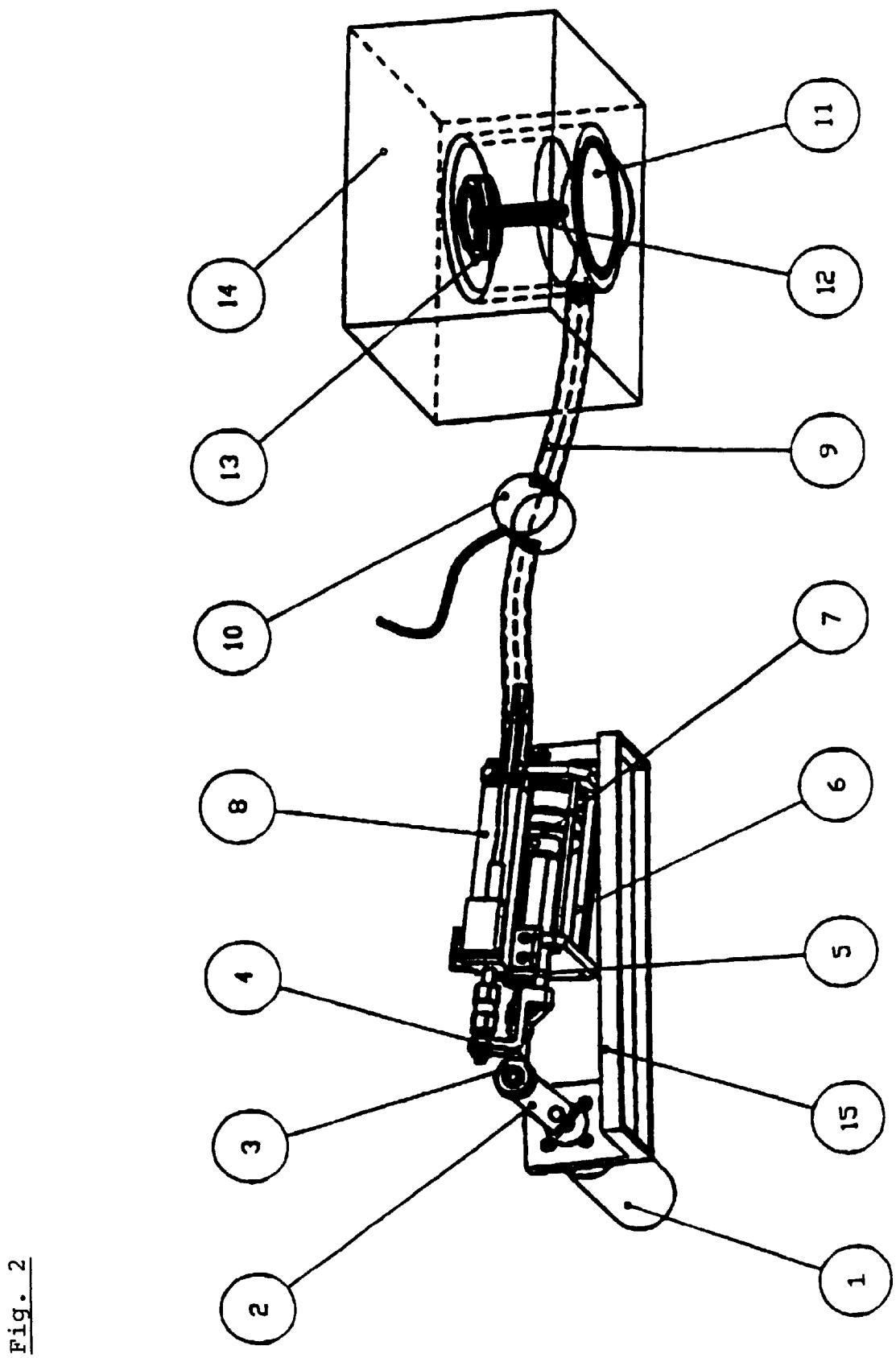
FIG. 2: a perspective view of the pumping device according to the present invention with the piston unit and the membrane unit.

FIG. 2 shows a perspective view of the pumping device according to the present invention with driving device 1 which is designed as an electric gear motor. Control lever 2 transmits the rotation of the gear motor to piston 7 by means of the self-contained cardan joint 3.

The piston rod of piston 7 has a locking element 5 mounted on a flange 4. In addition, measuring device 8, designed as a path sensor, is also mounted on flange 4.

Piston 7, designed as a precision piston, with the piston rod runs in a precision cylinder 6 with a pump cover and a tension rod.

The movements of piston 7 are transmitted to membrane unit 14 by hydraulic unit 9, which is designed as a line in the present embodiment. This membrane unit has membrane 11 bordering the first chamber 13. First chamber 13 contains vent valve 12 according to the present embodiment. If gases collect in hydraulic unit 9, they are removed from the hydraulic unit by vent valve 12, so that an incompressible transmission medium is always available between the piston unit and the membrane unit.

Pressure sensor 10, which is located in hydraulic unit 9, which is filled with hydraulic fluid, is connected to a display and/or driving device 1 by a computer integrated into the control unit 16, turning the device off on reaching or exceeding a definable limit value. This reliably limits the maximum pressure head in the entire system in the event of a blockade of hydraulic unit 9 or a defect in the valves or clamps of the head piece, for example.

To improve the handling of the pumping device according to the present invention, the piston unit with driving device 1 is mounted on a chassis 15.

A membrane pump head, designed as a disposable article is placed on membrane unit 14 in a manner not shown here and thus forms the second chamber, which is bordered by membrane 11 of membrane unit 14, for example.

Figure 3:
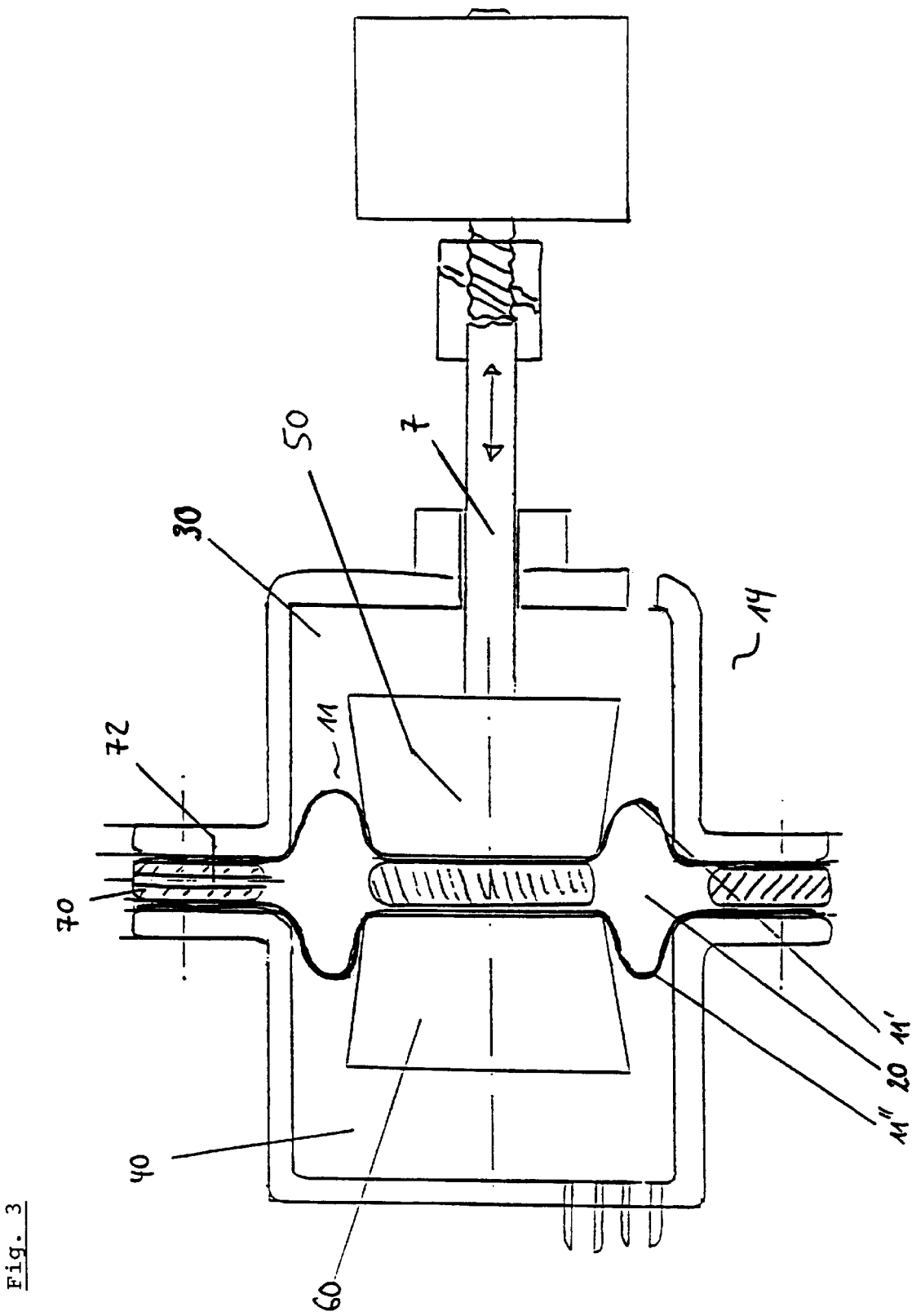
FIG. 3: a sectional diagram through a pumping device according to the present invention with a membrane unit having a two-layer membrane.

FIG. 3 shows a sectional diagram through a pumping device according to the present invention with a membrane unit 14 having a two-layer membrane 11. Membrane 11 consists of membrane layers 11' and 11" bordering interspace.20. Both membrane layers 11', 11" are made of a non-stretching material, e.g., reinforced by a woven fabric. Interspace 20 is filled with an incompressible medium such as oil.

The volumes of the first chamber 30 and chamber 40 arranged on the opposite side of membrane 11 remain constant regardless of the pressure gradient prevailing between the two chambers 30, 40. Consequently, this prevents the deflections that occur with known membranes due to a pressure difference across the membrane, which would thus lead to a mistaken relationship between piston position and membrane deflection.

A movement of piston 7 of the piston unit leads to displacement of the interspace 20 according to the present invention without altering its volume. A change in volume in chamber 40 is produced exclusively by the movement of piston 7 and the end piece 50 connected to it. Support 60 is provided on the side of membrane 11 facing chamber 40 to secure membrane layer 11".

Membrane layers 11', 11" are arranged so that they are separated by spacer 70. Spacer 70 has an orifice 72 which serves to fill interspace 20 with a suitable incompressible medium.

The pumping device according to the present invention is a pumping, balancing and metering system for medical fluids such as blood and dialysis fluids which functions reliably and is easy to handle. It can be used to particular advantage in the field of peritoneal dialysis, hemodialysis, hemofiltration and related methods. Due to the combination and connection of a piston unit with a measuring device and a membrane unit by means of a hydraulic unit, the good properties of piston systems, extending in particular to accurate metering, are guaranteed, with the advantages of a membrane unit that permits a reliable separation of working media and delivery media, as a result of which the measuring device according to the present invention permits accurate metering and balancing.

What is claimed is:

1. A pumping device for delivering and metering medical fluids comprising:
   a. a membrane unit having a membrane bordering a first chamber;
   b. a pumping unit connected to the first chamber by a hydraulic unit containing hydraulic fluid that is in fluid connection with the first chamber;
   c. a hydraulic sensor in fluid connection with the hydraulic unit, the hydraulic sensor adapted and arranged for measuring the pressure of the fluid within the hydraulic unit;
   d. a measuring device for measuring the pumping unit output; and
   e. a control unit connected to the measuring device, the pumping unit, and the hydraulic sensor; wherein the control unit is adapted and arranged for controlling the pumping unit output based on the measurements of the measuring device, and wherein the control unit is adapted for shutting off the pumping unit in response to a measured pressure outside a predetermined range.

2. The device of claim 1, wherein the pumping unit output is selected from the group consisting of the metering rate and quantity of fluid.

3. The device of claim 1, wherein the pumping unit has a driving device and a piston.

4. The device of claim 3, wherein the piston includes a piston head and a piston shaft.

5. The device of claim 4, wherein the measuring device is adapted to measure the pumping unit output by determining the axial position of the piston.

6. The device of claim 1 where the measuring device includes sensors selected from the group consisting of optical, electromechanical and electrical sensors.

7. The device of claim 3, wherein the piston is arranged on a chassis.

8. The device of claim 1, wherein the membrane has a first and a second layer of a non-stretching material forming an interspace therebetween, the interspace being filled with a non-compressible medium such that the membranes have an outward bulge.

9. The device of claim 8, wherein the non-compressible medium is a spacer.

10. The device of claim 4, wherein the measuring device is adapted and arranged to determine the axial position of the piston shaft.

11. The device of claim 2, further comprising a computer connected to the measuring device and the control unit, wherein the computer is adapted for calculating parameters for the pumping device, wherein the parameters are selected from the group consisting of volume of fluid delivered, metering rate or delivery rate.

12. The device of claim 3, wherein the driving device includes a linear drive.

13. The device of claim 12, wherein the linear drive is selected from the group consisting of eccentric drives, spindle drivers, rack and pinion drives, pneumatic pistons and compressor drives.

14. The device of claim 1 wherein the hydraulic unit includes a vent valve.

15. The device of claim 11 wherein the computer is integrated into the control unit.

16. A pumping device for delivering and metering medical fluids comprising:

a. a membrane unit having a first membrane bordering a first chamber;

b. a membrane pump head mounted on the membrane unit, the membrane pump head having a second chamber bordered by the first membrane on the side opposite the first chamber, the second chamber having an inlet and an outlet for conveying medical fluids;

c. a pumping unit connected to the first chamber by a hydraulic unit containing hydraulic fluid in fluid connection with the first chamber;

d. a hydraulic sensor in fluid connection with the hydraulic unit, the hydraulic sensor adapted and arranged for measuring the pressure of the fluid within the hydraulic unit;

e. a measuring device for measuring the pumping unit output; and f. a control unit connected to the measuring device, the pumping unit, and the hydraulic sensor, wherein the control unit is adapted and arranged for controlling the pumping unit output based on the measurements of the measuring device, and wherein the control unit is adapted for shutting off the pumping unit in response to a measured pressure outside a predetermined range;

wherein movement of fluid in the first chamber induces movement of fluid in the second chamber.

17. The device of claim 16, wherein the membrane pump head is detachably mounted on the membrane unit.

* * * * *

UNITED STATES PATENT AND TRADEMARK OFFICE
CERTIFICATE OF CORRECTION

PATENT NO. : 6,672,841 C1
APPLICATION NO. : 90/008871
DATED : October 28, 2008
INVENTOR(S) : Herklotz et al.

It is certified that error appears in the above-identified patent and that said Letters Patent is hereby corrected as shown below:

On the Title page, item [75]:

The first-named inventor should be changed from "Martin Hertklotz" to --Martin Herklotz--.

Page 2, below Other Publications, column 2, line 9 "Peritroneal Dialyser" should be changed to --Peritoneal Dialyser--;

Column 2, line 17 (Claim 34, line 1), "inicudes" should be changed to --includes--.

Signed and Sealed this

Nineteenth Day of May, 2009

JOHN DOLL
*Acting Director of the United States Patent and Trademark Office*

EX PARTE REEXAMINATION CERTIFICATE (6491st)
United States Patent
Hertklotz et al.

(10) Number: US 6,672,841 C1
(45) Certificate Issued: Oct. 28, 2008

(54) PUMPING AND METERING DEVICE

(75) Inventors: Martin Hertklotz, Griesheim (DE); Hans-Peter Schneider, Neu-Anspach (DE); Jörg Bigalke, Frankfurt (DE); Rainer Dönig, Franfurt (DE); Jürgen Häcker, Weinsberg (DE)

(73) Assignee: Fresenius Medical Care Deutschland GmbH, Bad Homburg (DE)

Reexamination Request:
No. 90/008,871, Oct. 9, 2007

Reexamination Certificate for:
Patent No.: 6,672,841
Issued: Jan. 6, 2004
Appl. No.: 09/308,914
Filed: Nov. 18, 1999

(22) PCT Filed: Mar. 26, 1998

(86) PCT No.: PCT/EP98/01792
§ 371 (c)(1),
(2), (4) Date: Nov. 18, 1999

(87) PCT Pub. No.: WO99/17019
PCT Pub. Date: Apr. 8, 1999

(51) Int. Cl.
*F04B 49/00* (2006.01)

(52) U.S. Cl. .................. 417/46; 417/386; 417/388; 417/390; 417/395; 60/539; 60/535

(58) Field of Classification Search .................. None
See application file for complete search history.

(56) References Cited

U.S. PATENT DOCUMENTS

| | | | |
|---|---|---|---|
| 2,409,734 A | 10/1946 | Bucher | |
| 2,766,907 A | 10/1956 | Wallace, Jr. | |
| 3,023,750 A | 3/1962 | Baron | |
| 3,153,414 A | 10/1964 | Beall et al. | |
| 3,218,979 A | 11/1965 | Baldwin | |
| 3,428,042 A | * 2/1969 | Chesnut | 600/17 |
| 3,430,731 A | 3/1969 | Satzinger | |
| 3,620,215 A | 11/1971 | Tysk et al. | |
| 3,656,873 A | 4/1972 | Schiff | |
| 3,730,183 A | 5/1973 | Goldsmith | |
| 3,774,762 A | 11/1973 | Lichtenstein | |
| 3,912,455 A | 10/1975 | Lichtenstein | |
| 3,946,731 A | 3/1976 | Lichtenstein | |
| 3,955,901 A | 5/1976 | Hamilton | |

(Continued)

FOREIGN PATENT DOCUMENTS

| | | |
|---|---|---|
| WO | WO 90/13795 | 11/1990 |
| WO | WO 93/09828 | 5/1993 |
| WO | WO 94/20153 | 9/1994 |

(Continued)

OTHER PUBLICATIONS

Bergstrom et al., An Automated Apparatus for Peritoneal Dialysis with Volumetric Fluid Balance Measurement, reprinted from Dialysis & Transplantation, Jun./Jul. 1976.
Brochure entitled "For Volume Measurement, Temperature Control and Cycling of Dialsying Fluid, Peritoneal Dialyser PD700," 1970.

(Continued)

*Primary Examiner*—Jeffrey R Jastrzab

(57) ABSTRACT

The present invention relates to a pumping device for delivering and metering fluids, in particular medical fluids such as dialysis fluids, with a piston unit having a driving device and a piston and with a membrane unit which has a membrane and a first chamber bordered by the membrane. The pumping device also has a hydraulic unit which has a space to accommodate a hydraulic fluid which is connected to the piston of the piston unit and to the first chamber of the membrane unit. The reliability of metering by such a pumping device is increased by providing a control unit for guaranteeing a predefinable metering rate and/or quantity and also providing a measuring device by means of which the axial position of the piston unit can be determined directly and which can be connected to the control unit.

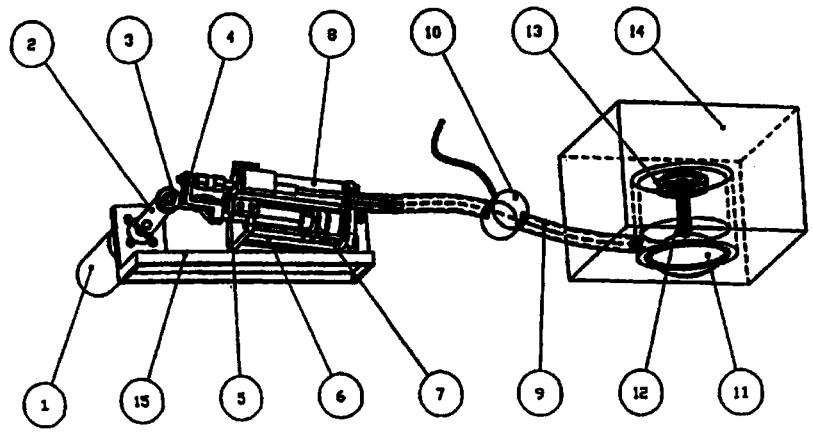

U.S. PATENT DOCUMENTS

| Patent | Date | Name |
|---|---|---|
| 4,048,994 A | 9/1977 | Lo |
| 4,136,708 A | 1/1979 | Cosentino |
| 4,236,880 A | 12/1980 | Archibald |
| 4,237,881 A | 12/1980 | Beigler et al. |
| 4,273,121 A | 6/1981 | Jassawalla |
| 4,303,376 A | 12/1981 | Siekmann |
| 4,370,983 A | 2/1983 | Lichtenstein |
| 4,379,453 A | 4/1983 | Baron |
| 4,416,596 A | 11/1983 | Lichtenstein |
| 4,430,078 A | 2/1984 | Sprague |
| 4,441,603 A | 4/1984 | Baumard |
| 4,464,172 A | 8/1984 | Lichtenstein |
| 4,479,760 A | 10/1984 | Bilstad et al. |
| 4,479,761 A | 10/1984 | Bilstad et al. |
| 4,479,762 A | 10/1984 | Bilstad et al. |
| 4,507,116 A | 3/1985 | Leibinsohn |
| 4,539,005 A | 9/1985 | Greenblatt |
| 4,552,552 A | 11/1985 | Polaschegg et al. |
| 4,573,968 A | 3/1986 | Parker |
| 4,613,327 A | 9/1986 | Tegrarian et al. |
| 4,624,625 A * | 11/1986 | Schrenker .................. 417/20 |
| 4,634,430 A | 1/1987 | Polaschegg |
| 4,778,451 A | 10/1988 | Kamen |
| 4,804,360 A | 2/1989 | Kamen |
| 4,808,161 A | 2/1989 | Kamen |
| 4,816,019 A | 3/1989 | Kamen |
| 4,826,482 A | 5/1989 | Kamen |
| 4,830,586 A | 5/1989 | Herter et al. |
| 4,886,432 A | 12/1989 | Kimberlin |
| 4,923,612 A | 5/1990 | Trivett et al. |
| 4,976,162 A | 12/1990 | Kamen |
| 5,056,036 A * | 10/1991 | Van Bork .................. 700/282 |
| 5,074,755 A * | 12/1991 | Vincent ....................... 417/18 |
| 5,088,515 A | 2/1992 | Kamen |
| 5,116,021 A | 5/1992 | Faust et al. |
| 5,178,182 A | 1/1993 | Kamen |
| 5,188,515 A | 2/1993 | Horn |
| 5,193,990 A | 3/1993 | Kamen et al. |
| 5,195,986 A | 3/1993 | Kamen |
| 5,211,201 A | 5/1993 | Kamen et al. |
| 5,222,946 A | 6/1993 | Kamen |
| 5,241,985 A | 9/1993 | Faust et al. |
| 5,324,422 A | 6/1994 | Colleran et al. |
| 5,326,476 A | 7/1994 | Grogan et al. |
| 5,344,292 A | 9/1994 | Rabenau et al. |
| 5,349,852 A | 9/1994 | Kamen et al. |
| 5,350,357 A | 9/1994 | Kamen et al. |
| 5,353,837 A | 10/1994 | Faust |
| 5,364,371 A | 11/1994 | Kamen |
| 5,401,342 A | 3/1995 | Vincent et al. |
| 5,421,823 A | 6/1995 | Kamen et al. |
| 5,428,510 A | 6/1995 | Shirai et al. |
| 5,431,626 A | 7/1995 | Bryant et al. |
| 5,431,823 A | 7/1995 | Gofer |
| 5,438,510 A | 8/1995 | Bryant et al. |
| 5,474,683 A | 12/1995 | Bryant et al. |
| 5,476,368 A | 12/1995 | Rabenau et al. |
| 5,487,649 A | 1/1996 | Dorsey, III et al. |
| 5,526,844 A | 6/1996 | Kamen et al. |
| 5,533,389 A | 7/1996 | Kamen et al. |
| 5,540,808 A | 7/1996 | Vincent et al. |
| 5,575,310 A | 11/1996 | Kamen et al. |
| 5,628,908 A | 5/1997 | Kamen et al. |
| 5,634,896 A | 6/1997 | Bryant et al. |
| 5,641,892 A | 6/1997 | Larkins et al. |
| 5,647,733 A | 7/1997 | Augustyn |
| 5,669,764 A | 9/1997 | Behringer et al. |
| 5,713,865 A | 2/1998 | Manning et al. |
| 5,755,683 A | 5/1998 | Houle et al. |
| 5,772,637 A | 6/1998 | Heinzmann et al. |
| 5,782,575 A | 7/1998 | Vincent et al. |
| 5,826,844 A | 10/1998 | Purdy |
| 5,935,105 A | 8/1999 | Manning et al. |
| 5,938,634 A | 8/1999 | Packard |
| 5,989,423 A | 11/1999 | Kamen et al. |
| 6,001,201 A | 12/1999 | Vincent et al. |
| 6,165,154 A | 12/2000 | Gray et al. |
| 6,210,361 B1 | 4/2001 | Kamen et al. |
| 6,234,997 B1 | 5/2001 | Kamen et al. |
| 6,276,656 B1 | 8/2001 | Baresich |
| 6,364,857 B1 | 4/2002 | Gray et al. |
| 6,406,276 B1 | 6/2002 | Normand et al. |
| 6,464,667 B1 | 10/2002 | Kamen et al. |
| 6,709,417 B1 | 3/2004 | Houle et al. |
| 6,726,656 B2 | 4/2004 | Kamen et al. |
| 7,214,210 B2 | 5/2007 | Kamen et al. |
| 2001/0007932 A1 | 7/2001 | Kamen |
| 2006/0241550 A1 | 10/2006 | Kamen et al. |
| 2007/0085049 A1 | 4/2007 | Houle et al. |

FOREIGN PATENT DOCUMENTS

| | | |
|---|---|---|
| WO | WO 94/20155 | 9/1994 |
| WO | WO 94/20156 | 9/1994 |
| WO | WO 94/20157 | 9/1994 |
| WO | WO 94/20158 | 9/1994 |
| WO | WO 96/40328 | 12/1996 |
| WO | WO 96/40330 | 12/1996 |
| WO | WO 96/40341 | 12/1996 |
| WO | WO 96/41156 | 12/1996 |
| WO | WO 99/10028 | 3/1999 |

OTHER PUBLICATIONS

Brochure entitled "Peritoneal Dialyser PD700," May 1979.

Operating Instructions, Peritoneal Dialyser PD700, For Ser. No. 300.

PD 1001: A Wide Range of Treatments and Possibilities in Future Clinical Application, Peritoneal Dialysis International, Oct. 1–4, 1992, vol. 13, Supplement 2.

PD700 Peritoneal Dialyser Users Handbook, Dec. 1977.

Peritoneal Dialyser PD700 Instruction Manual.

Peritroneal Dialyser PD700 Service Manual, Jun. 1977.

Programming an Automated Peritoneal Dialysis Treatment with the PD 1001, Peritoneal Dialysis International, Oct. 1–4, 1992, vol. 13, Supplement 2.

Technical Note PD700 Peritoneal Dialyser, Jan. 29, 1979.

Piazolo et al., Erfahrungen mit einem neuen vollautomatischen Peritoneal–dialysegerat, Munchener Medizinische Wochenschrift, 1972.

Skotselanvisning for Peritoneal—Dialysapparat PD700.

U. Callsen, Peritoneal–Dialysator PD700, Prakt. Anasth. 9 (1974) 119–120.

U.S. Appl. No. 07/614,806, filed Nov. 19, 1990, entitled: Integral Intravenous Fluid Delivery Device.

U.S. Appl. No. 07/615,612, filed Nov. 19, 1990, entitled: Acoustic Volume Measurement with Fluid Management Capability.

U.S. Appl. No. 07/673,834, filed Mar. 22, 1991, entitled: Membrane–Based Rotary Peristaltic Pump.

U.S. Appl. No. 07/673,835, filed Mar. 22, 1992, entitled: Constant–Pressure Fluid Supply System.

U.S. Appl. No. 07/674,813, filed Mar. 22, 1991, entitled: Flow–Control Valve System.

U.S. Appl. No. 07/748,346, filed Aug. 22, 1991, entitled: Constant–Pressure Fluid Supply System with Multiple Fluid Capability.

U.S. Appl. No. 07/847,500, filed Mar. 11, 1992, entitled: Membrane–Based Rotary Peristaltic Pump.

U.S. Appl. No. 08/027,484, filed Mar. 3, 1993, entitled: Peritoneal Dialysis Systems and Methods Employing a Liquid Distribution and Pump Cassette with Self–Contained Air Isolation and Removal.

U.S. Appl. No. 08/443,428, filed May 18, 1995, entitled: Pump Controller Using Acoustic Spectral Analysis.

U.S. Appl. No. 08/916,890, filed Aug. 22, 1997, entitled: System, Method and Cassette for Mixing and Delivering Intravenous Drugs.

* cited by examiner

US 6,672,841 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–17 is confirmed.

New claims 18–53 are added and determined to be patentable.

18. The device of claim 16, wherein the membrane pump head is disposable.

19. The device of claim 16, wherein the membrane pump head is adapted for one-time use.

20. The device of claim 16, wherein the membrane pump head is disposable and adapted for one-time use.

21. The device of claim 16, wherein the pumping unit further comprises a piston.

22. The device of claim 21, wherein the measuring device is adapted to measure the pumping unit output by determining an axial position of the piston.

23. The device of claim 21, wherein the measuring device is adapted and arranged to determine an axial position of the piston.

24. A pumping device for delivering and metering medical fluids comprising:
  a. a membrane unit having a first membrane bordering a first chamber;
  b. a membrane pump head detachably mounted on the membrane unit, the membrane pump head having a second membrane bordering a second chamber, wherein the second membrane is disposed adjacent to the first membrane when the membrane pump head is mounted on the membrane unit;
  c. a pumping unit connected to the first chamber by a hydraulic unit containing hydraulic fluid that is in fluid connection with the first chamber;
  d. a hydraulic sensor in fluid connection with the hydraulic unit, the hydraulic sensor adapted and arranged for measuring the pressure of the hydraulic fluid within the hydraulic unit;
  e. a measuring device for measuring the pumping unit output; and
  f. a control unit connected to the measuring device, the pumping unit, and the hydraulic sensor, wherein the control unit is adapted and arranged for controlling the pumping unit output based on the measurements of the measuring device, and wherein the control unit is adapted for shutting off the pumping unit in response to a measured pressure outside a predetermined range.

25. The device of claim 24, wherein the membrane pump head is disposable.

26. The device of claim 24, wherein the membrane pump head is adapted for one-time use.

27. The device of claim 24, wherein the membrane pump head is disposable and adapted for one-time use.

28. The device of claim 24, wherein the second chamber further comprises an inlet and an outlet for conveying medical fluids.

29. The device of claim 24, wherein movement of fluid in the first chamber induces movement of fluid in the second chamber.

30. The device of claim 24, wherein the pumping unit output is selected from the group consisting of: a metering rate and a quantity of fluid.

31. The device of claim 24, wherein the pumping unit further comprises a driving device and a piston.

32. The device of claim 31, wherein the driving device comprises a linear drive.

33. The device of claim 32, wherein the linear drive is selected from the group consisting of: eccentric drives, spindle drives, rack and pinion drives, pneumatic pistons and compressor drives.

34. The device of claim 31, wherein the piston inlcudes a piston head and a piston shaft.

35. The device of claim 24, wherein the measuring device is adapted and arranged to determine an axial position of the piston shaft.

36. The device of claim 24, wherein the measuring device includes one or more sensors selected from the group consisting of: optical, electromechanical and electrical sensors.

37. The device of claim 24, further comprising a computer connected to the measuring device and the control unit, wherein the computer is adapted to calculate one or more parameters for the pumping device, wherein the parameters are selected from the group consisting of: a volume of fluid delivered, a metering rate or a delivery rate.

38. The device of claim 37, wherein the computer is integrated into the control unit.

39. The device of claim 24, wherein the hydraulic unit comprises a vent valve.

40. A pumping device for delivering and metering medical fluids comprising:
  a. a membrane unit having a first membrane bordering a first chamber;
  b. a membrane pump head detachably mounted on the membrane unit, the membrane pump head having a second chamber bordered by the first membrane on the side opposite the first chamber, the second chamber having an inlet and an outlet for conveying medical fluids, wherein the membrane pump head is disposable;
  c. a pumping unit connected to the first chamber by a hydraulic unit containing hydraulic fluid in fluid connection with the first chamber;
  d. a hydraulic sensor in fluid connection with the hydraulic unit, the hydraulic sensor adapted and arranged for measuring the pressure of the hydraulic fluid within the hydraulic unit;
  e. a measuring device for measuring a pumping unit output; and
  f. a control unit connected to the measuring device, the pumping unit, and the hydraulic sensor, wherein the control unit is adapted and arranged for controlling the pumping unit output based on the measurements of the measuring device, and wherein the control unit is adapted for shutting off the pumping unit in response to a measured pressure outside a predetermined range;
  wherein movement of fluid in the first chamber induces movement of fluid in the second chamber when the membrane pump head is mounted on the membrane unit.

41. The device of claim 40, wherein the membrane pump head is adapted for one-time use.

42. The device of claim 40, wherein the pumping unit output is selected from the group consisting of: a metering rate and a quantity of fluid.

43. The device of claim 40, wherein the pumping unit further comprises a driving device and a piston.

44. The device of claim 43, wherein the driving device comprises a linear drive.

45. The device of claim 44, wherein the linear drive is selected from the group consisting of: eccentric drives, spindle drives, rack and pinion drives, pneumatic pistons and compressor drives.

46. The device of claim 43, wherein the piston comprises a piston head and a piston shaft.

47. The device of claim 46, wherein the measuring device is adapted and arranged to determine an axial position of the piston shaft.

48. The device of claim 40, wherein the measuring device comprises one or more sensors selected from the group consisting of: optical, electromechanical and electrical sensors.

49. The device of claim 40, further comprising a computer connected to the measuring device and the control unit, wherein the computer is adapted for calculating one or more parameters for the pumping device, wherein the parameters are selected from the group consisting of: a volume of fluid delivered, a metering rate, or a delivery rate.

50. The device of claim 49, wherein the computer is integrated into the control unit.

51. The device of claim 40, wherein the hydraulic unit comprises a vent valve.

52. The device of claim 1, wherein the hydraulic fluid within the hydraulic unit is an incompressible medium.

53. The device of claim 1, wherein the hydraulic fluid within the hydraulic unit is an incompressible liquid.

* * * * *